(12) United States Patent
Gensch (10) Patent No.: US 11,166,869 B2
(45) Date of Patent: Nov. 9, 2021

(54) COOLING COMPRESSION SLEEVE

(71) Applicant: CoolCorp, Inc., Pierceton, IN (US)

(72) Inventor: Richard Wesley Gensch, Pierceton, IN (US)

(73) Assignee: CoolCorp, Inc., Pierceton, IN (US)

( * ) Notice: Subject to any disclaimer, the term of this patent is extended or adjusted under 35 U.S.C. 154(b) by 445 days.

(21) Appl. No.: 15/649,783

(22) Filed: Jul. 14, 2017

(65) Prior Publication Data

US 2018/0014995 A1    Jan. 18, 2018

Related U.S. Application Data (60) Provisional application No. 62/362,477, filed on Jul. 14, 2016.

(51) Int. Cl.
 *A61H 9/00* (2006.01)
 *A61F 7/02* (2006.01)
 (Continued)

(52) U.S. Cl.
 CPC ............. *A61H 9/0078* (2013.01); *A61F 7/02* (2013.01); *A61F 7/10* (2013.01); *A61H 9/0085* (2013.01);
 (Continued)

(58) Field of Classification Search
 CPC .. A61H 9/0078; A61H 9/0085; A61H 9/0092; A61H 2201/0214; A61H 2201/0103; A61H 2201/0157; A61H 2201/0278; A61H 2201/1635; A61H 2201/0207; A61H 2201/1638; A61H 2201/164; A61H 2201/1642; A61H 2201/1645; A61H 2201/165; A61H 2205/062; A61H 2205/102; A61H 2205/06; A61H 2205/10; A61H 2205/106; A61H 2205/108; A61F 7/00; A61F 7/02; A61F 7/10; A61F 7/106; A61F 2007/0091; A61F 2007/0215; A61F 2007/0029-0034; A61F 2007/0039; A61F 2007/0041-0043; A61F 2007/0056; A61F 2007/0219; A61F 2007/022-0223; A61F 2007/0225; A61F 2007/0231; A61F 2007/0246-0249; A61F 2007/0253; A61F 2007/0257; A61F 2007/026; A61F 2007/0268; A61F 2007/108; A61F 2007/0244; A61F 2007/0001; A61F 2007/023;
 (Continued)

(56) References Cited

U.S. PATENT DOCUMENTS

3,628,537 A * 12/1971 Berndt ..................... A61F 7/10
                                                              607/112
3,901,225 A    8/1975 Sconce
(Continued)

*Primary Examiner* — Justine R Yu
*Assistant Examiner* — Benjamin M. Kusiak
(74) *Attorney, Agent, or Firm* — Taylor IP, P.C.

(57) ABSTRACT

A cooling compression sleeve device generally including three layers, a flexible bottom layer, a flexible middle layer, and a flexible top layer, and two voids, the first void substantially filled with a cooling agent and the second void including a selectively inflatable air bladder, which in its preferred form is portable, cleanable, reusable, and useful to provide cooling therapy to the limbs of humans or animals and particularly to the knee, shoulder, and elbow joints.

18 Claims, 6 Drawing Sheets

(51) Int. Cl.
*A61F 7/10* (2006.01)
*A61F 7/00* (2006.01)

(52) U.S. Cl.
CPC . *A61F 2007/003* (2013.01); *A61F 2007/0032* (2013.01); *A61F 2007/0042* (2013.01); *A61F 2007/0091* (2013.01); *A61F 2007/0215* (2013.01); *A61F 2007/0231* (2013.01); *A61F 2007/0247* (2013.01); *A61F 2007/0257* (2013.01); *A61H 2201/0214* (2013.01); *A61H 2205/062* (2013.01); *A61H 2205/102* (2013.01)

(58) Field of Classification Search
CPC ........ A61F 2007/0282; A61F 2007/101; A61F 2007/103; A61B 5/00; A61B 5/02; A61B 5/022; A61B 17/135; F16K 7/061
USPC .......... 601/18, 84, 148, 151; 602/13, 14, 20, 602/23, 36, 2; 600/490, 495, 498, 499; 251/4–10; 285/90, 238, 242, 245
See application file for complete search history.

(56) References Cited

U.S. PATENT DOCUMENTS

| | | | | |
|---|---|---|---|---|
| 5,423,996 | A * | 6/1995 | Salyer | C09K 5/063 |
| | | | | 252/70 |
| 5,868,690 | A * | 2/1999 | Eischen, Sr. | A61H 9/0085 |
| | | | | 601/151 |
| 6,695,872 | B2 * | 2/2004 | Elkins | A41D 13/005 |
| | | | | 607/104 |
| 7,837,638 | B2 * | 11/2010 | Miros | A61F 5/0106 |
| | | | | 602/13 |
| 7,896,910 | B2 * | 3/2011 | Schirrmacher | A61F 7/02 |
| | | | | 607/104 |
| 8,876,875 | B1 * | 11/2014 | Nilforushan | A61F 7/02 |
| | | | | 607/108 |
| 9,170,059 | B2 * | 10/2015 | Johnson | F28F 3/12 |
| 2004/0098035 | A1 * | 5/2004 | Wada | A61B 17/1325 |
| | | | | 606/201 |
| 2007/0152442 | A1 * | 7/2007 | Cleveland | F16L 13/141 |
| | | | | 285/256 |
| 2008/0119745 | A1 * | 5/2008 | Yang | A61B 5/02141 |
| | | | | 600/493 |
| 2012/0209153 | A1 * | 8/2012 | Farrow | A61H 9/0092 |
| | | | | 601/18 |
| 2013/0253383 | A1 * | 9/2013 | Maxon-Maldonado | |
| | | | | A61F 7/00 |
| | | | | 601/15 |
| 2014/0231280 | A1 * | 8/2014 | Chou | A61F 7/086 |
| | | | | 206/205 |
| 2014/0300099 | A1 * | 10/2014 | Lehmann | F16L 37/113 |
| | | | | 285/91 |
| 2015/0073326 | A1 * | 3/2015 | Shih | A61F 7/0085 |
| | | | | 602/53 |
| 2015/0114858 | A1 * | 4/2015 | Rothenberg | F25D 5/02 |
| | | | | 206/222 |
| 2015/0173432 | A1 * | 6/2015 | McCoy | A41D 13/0056 |
| | | | | 62/259.3 |
| 2015/0366474 | A1 * | 12/2015 | Pearson | A61B 5/7415 |
| | | | | 600/438 |
| 2016/0051404 | A1 * | 2/2016 | Choucair | A61F 7/10 |
| | | | | 607/114 |
| 2016/0100978 | A1 * | 4/2016 | Rose | A61F 7/02 |
| | | | | 601/18 |
| 2016/0255884 | A1 * | 9/2016 | Chaumont | A01K 13/008 |
| 2016/0262929 | A1 * | 9/2016 | Rodao | A61F 7/10 |
| 2016/0324722 | A1 * | 11/2016 | Sinderby | B60K 15/04 |
| 2016/0354232 | A1 * | 12/2016 | Rozental | A61F 7/10 |
| 2017/0105870 | A1 * | 4/2017 | Yazdani | A41D 13/005 |
| 2017/0231512 | A1 * | 8/2017 | Li | A61B 5/02233 |
| | | | | 600/499 |
| 2017/0273824 | A1 * | 9/2017 | Gannon | A61F 7/02 |
| 2018/0325723 | A1 * | 11/2018 | Shih | A61F 7/007 |

\* cited by examiner

COOLING COMPRESSION SLEEVE

CROSS REFERENCE TO OTHER APPLICATIONS

This Application claims priority to and incorporates fully by reference U.S. Provisional Application No. 62/362,477, Cooling Compression Sleeve, filed on Jul. 14, 2016.

STATEMENT REGARDING FEDERALLY SPONSORED RESEARCH OR DEVELOPMENT

Not applicable.

BACKGROUND

The present invention is directed generally to a device for providing cooling therapy, and, optionally, compression therapy, to a human or animal suffering sore muscles or joints or athletic injury, to a human or animal seeking to avoid an athletic or overuse injury, or to a human or animal recovering from surgery or other injury.

Cooling therapy is used both as treatment for injury and as a prophylactic measure to prevent injury, and also to mitigate pain and inflammation in joints and muscles associated with strenuous use, and pain and inflammation caused by trauma, such as surgery. It is well known that cooling of an injury site (usually with ice) after injury, athletic use, overtraining, or trauma such as surgery can reduce swelling and inflammation and speed recovery. It is further known that cooling an uninjured site after use, such, as for example, cooling of the knee joints after running, can reduce the chances of future injury to that site. Cooling reduces pain, reduces inflammation, reduces tissue damage, and has also been shown to have a positive effect on athletic performance.

Cooling therapy is known to be particularly beneficial to human athletes or animals whose performance requires repetitive movement or imposes repeated mechanical stress on the same joint or joints. Baseball pitchers, for example, endure strenuous repeated use of the elbow and shoulder joints of their pitching arm. Runners, for example, endure strenuous repeated use of the knee and ankle joints. For further non-limiting example, animals used for sport or competition, such as horses used in racing, jumping, or hunting activities, are susceptible to injuries to the knee and ankle joints, which are often difficult to treat for such injured animals. Such athletes and animals often employ therapeutic strategies such as cooling to delay, mitigate, prevent, or treat injuries to specific joints or areas. Cooling therapy is also known to be particularly advantageous for post-surgical patients, whether human or animal, for whom cooling therapy can reduce post-surgical pain and inflammation and speed recovery.

In many cases, cooling therapy is needed on a limb, particularly at a site such as a knee, shoulder, or elbow. It is a known challenge in the art to provide adequate cooling to these areas without creating undue discomfort or inconvenience for the injured human or animal. For example, cooling therapy in its simplest form known to the art involves holding a cold object, such as an ice-filled towel, against the affected site. This form of cooling therapy has a number of disadvantages, however, such as requiring a user to hold a cold object during the entirety of the therapy session, denying the user the use of the hand holding the object and causing discomfort in the hand used to hold the cooling object. In a case where cooling therapy is applied to a knee, the injured human or animal is unlikely to be able to walk while the cold object is applied to the joint at the same time. And in general, this strategy is only able to cool a relatively small area at a time, such as one side of a joint or limb. Further, injured or post-surgical patients may in some cases not possess sufficient mobility to employ this strategy, as they may be unable to hold the cold object in place for an adequate period of time. In a case where cooling therapy is applied to an injured animal, a human may be required to hold the cold object in contact with the animal for the duration of the therapy session, often while attempting to limit or restrain movement of the injured limb by the animal.

Committed athletes, such as those at the professional and collegiate levels, routinely seek the benefits of cooling therapy by using ice baths. Ice baths are for many such athletes the cooling therapy strategy of choice, and are employed after most training sessions and competitions. Ice baths can take the form of large tubs filled with cold water, often supplemented with ice. Other systems are available that feature tubs of water actively cycled through a cooling mechanism. To use the ice bath, athletes submerge themselves in the water at least until the site desired to be treated is underwater. Ice bath sessions routinely last for 10 to 15 minutes. Ice bath water temperature can vary, widely but generally ranges from several degrees above freezing to about 17° C. In all cases, ice bath cooling strategies require a user to endure significant discomfort, as the user must expose much more of their body to uncomfortably cold temperatures than is required by other strategies. Ice baths suffer additional disadvantages, such as the difficulty of maintaining a sufficiently low bath temperature during extended or repeated uses, and the difficulty of maintaining hygienic conditions in the bath after multiple athletes—often still sweaty or dirty from training or competition—have used it. Ice baths also deny a user the ability to walk or perform most other tasks during the therapy session, regardless of the location of the site being treated. Additionally, the use of ice baths is typically unsuitable for treatment of injured animals, as it may be exceptionally difficult or impossible to submerge an injured animal in such an ice bath for a sustained period of time.

SUMMARY

The present invention, in its various aspects, is directed to a device for providing cooling therapy to the limbs of humans or animals, and particularly to the knee, shoulder, and elbow joints, while allowing the human or animal receiving the cooling therapy to be mobile and to perform other tasks during the therapy session without significant limitation and without creating discomfort in other areas of the body. The present invention, in its various aspects, is also directed to a device for providing cooling therapy to the entire circumferential surface of a limb or joint while enjoying the aforementioned benefits. Although particular aspects and versions of the invention are discussed herein, the invention is not limited thereby, and additional aspects and versions will be apparent from this description and the drawings.

The present invention, in one illustrative embodiment, is a three-layered sleeve comprising a bottom layer, a middle layer connected to the bottom layer, and a top layer connected to the middle layer. A first void between the bottom layer and middle layer is filled with a disposable, or, preferably, reusable cooling agent, such as water, salt, and corn starch, antifreeze, an antifreeze/water mixture, a water/ammonium nitrate mixture, or a water/propylene glycol mixture or gel, as would be apparent to one skilled in the art. The cooling agent may be free flowing throughout the first void, or the first void may alternately be divided into chambers or, preferably, filled with a sponge, mesh, or other agent to ensure the relatively equal distribution of the cooling agent throughout the void.

A second void between the middle layer and top layer is deflatably inflatable using an air inflation means such as a valve, and/or, optionally, a pump assembly attached or attachable to the outer surface of the top layer. The sleeve materials are preferably selected, and the sleeve is preferably configured, so that the bottom layer has relatively high thermal conductivity, and the middle and/or top layers have relatively high thermal insulation. When the sleeve is in place on a user's joint or limb, inflation of the second void compresses the sleeve to force the cooling agent into close contact with the bottom layer and the bottom layer into close contact with the limb, providing cooling to substantially the entirety of the circumferential surface of the area of desired treatment.

BRIEF DESCRIPTION OF THE DRAWINGS

The invention is disclosed in respect to, but not limited to, the various embodiments disclosed in the drawings accompanying herewith, wherein.

DESCRIPTION OF EMBODIMENTS

In a preferred embodiment, the present invention consists of a tubular sleeve with three layers, that is in this preferred form portable, cleanable, reusable, and useful to provide cooling therapy to limbs and particularly to the shoulder, elbow, and knee joints.

Referring now to this preferred embodiment, the sleeve of the present invention comprises a flexible bottom layer 1. The bottom layer 1 has a first surface 3 and a second surface 5 opposite the first surface 3. The bottom layer 1 as a whole is composed of a material or materials selected for relatively high thermal conductivity to assist with cooling of the user's selected limb or joint. The first surface 3 is adapted for non-irritating contact with the skin of a user, and preferably for prolonged contact of 15 minutes or more. The first surface 3 is further composed substantially of a material suited to engage in such prolonged contact without causing undue irritation or damage to a user's skin. Suitable materials for the first surface 3 materials include cotton, microfiber, or other water absorbent materials common to clothing, as would be appreciated by one skilled in the art.

The second surface 5 is opposite the first surface 3 and resultantly faces an interior first void 7. The second surface 5 is adapted to form a surface substantially impermeable to a cooling agent 9 filling the first void 7. The impermeability of the second surface 5 may be achieved either through the selection of the material of its composition, or by the application of a suitable coating or film layer. Suitable materials for the second surface 5 include, but are not limited to, flexible silicone, neoprene, and other flexible water impermeable materials.

As will be apparent to one skilled in the art, the bottom layer 1 (as well as the middle layer 11 and top layer 25) of this invention may be composed of a single material, or may comprise a composite of multiple materials. And, whether a single material or a composite, the surfaces of the layers may optionally or additionally be coated with one or more films or coating to assist with the desired permeability, thermal conductivity, or other characteristics. For example, in the bottom layer 1, the first surface 3 and second surface 5 may be composed of different materials joined to each other, or the bottom layer 1 may be of homogenous construction, using a material suitable for prolonged skin contact, sufficiently impermeable, and providing desired thermal conductivity. In this preferred embodiment, the bottom layer 1 is a composite, with the first surface 3 comprising a cotton layer and the second surface 5 comprising a flexible silicone layer.

The first void 7 is substantially filled with a cooling agent 9. The first void 7 is configured to keep the cooling agent 9 substantially evenly disposed around the circumference of the sleeve when the sleeve is compressed in use. The first void 7 may comprise the entirety of the area between the second surface 5 of the bottom layer 1 and the third surface 13 of the middle layer 11. Alternately, the first void 7 may be divided into two, three, four, or more chambers 15 by the imposition of walls 17 connecting the second surface 5 to the third surface 13. Preferably, the first void 7 is filled with a flexible liquid-retaining agent 19 such as a mesh or sponge to assist with the even distribution of cooling agent 9 throughout the entirety of the first void 7.

The cooling agent 9 is a liquid, gel, or highly flexible and flowable solid that can be brought to a sufficiently low temperature to serve as a cooling agent 9 in cooling therapy and that has a sufficiently high specific heat to remain cool for at least ten, and preferably at least fifteen minutes, the duration of a typical therapy session, while in contact with the body heat exuded by a human or animal's limb. Suitable cooling agents 9 may include single-use chemicals, such as the water/ammonium nitrate mixtures used in disposable cooling packs known to the art. Preferably, the cooling agent 9 is reusable. Suitable reusable cooling agents 9 include, for example, water and water/propylene glycol mixtures and water/antifreeze mixtures and gels such as those used in reusable cooling packs. Other suitable disposable or reusable cooling agents 9 will be apparent to one skilled in the art.

Defining the outer circumference of the first void 7 is a flexible middle layer 11. The middle layer 11 preferably has relatively low thermal conductivity, so as to insulate the cooling agent 9 within the first void 7 from ambient environmental or atmospheric heat. The middle layer 11 comprises a third surface 13 facing the first void 7 and a fourth surface 21 opposite the third surface 13. The third surface 13 is adapted to be substantially impermeable to the cooling agent 9. Suitable materials for the third surface 13 include those same materials suitable for the second surface 5. The fourth surface 21 faces a second void 23, and is substantially impermeable to air. Suitable materials for the fourth surface 21 also include those suitable for the second surface 5. Preferably, the middle layer 11 is of homogenous construction and is made of flexible silicone such that both the third surface 13 and fourth surface 21 comprise flexible silicone.

The second void 23 is defined by the fourth surface 21 and by a flexible top layer 25, which comprises a fifth surface 27 facing the second void 23 and a sixth surface 29 opposite the fifth surface 27. The second void 23 comprises a selectively inflatable air bladder 31. When the sleeve is placed on a user's limb and the second void 23 is inflated, the middle layer 11 and bottom layer 1 are forced inward with the first surface 3 biased against a user's skin or clothing, compressing the sleeve and ensuring that the cooling agent 9 is in substantial thermal connection with substantially all of the circumference of the portion of the user's limb covered by the sleeve. When the second void 23 is deflated, the sleeve relaxes, allowing easy removal.

The fifth surface 27 is substantially impermeable to air. The sixth surface 29 faces the outer environment, and is adapted to resist the abrasions, collisions, and wear of clothing in normal use, and preferably is adapted to resist punctures of the second void 23 or first void 7. Like the bottom layer 1 and middle layer 11, the top layer 25 may be of homogenous or composite construction, and, in either case, may optionally achieve desired structural properties by coating, or, in the case of the sixth surface 29, covering with a cloth or a flexible or rigid protective shell. Preferably, the top layer 25 is of homogenous construction and is composed of nylon. The top layer 25 may optionally include one or more materials adapted to provide relatively low thermal conductivity and relatively high insulative properties to the layer.

Figure 6:
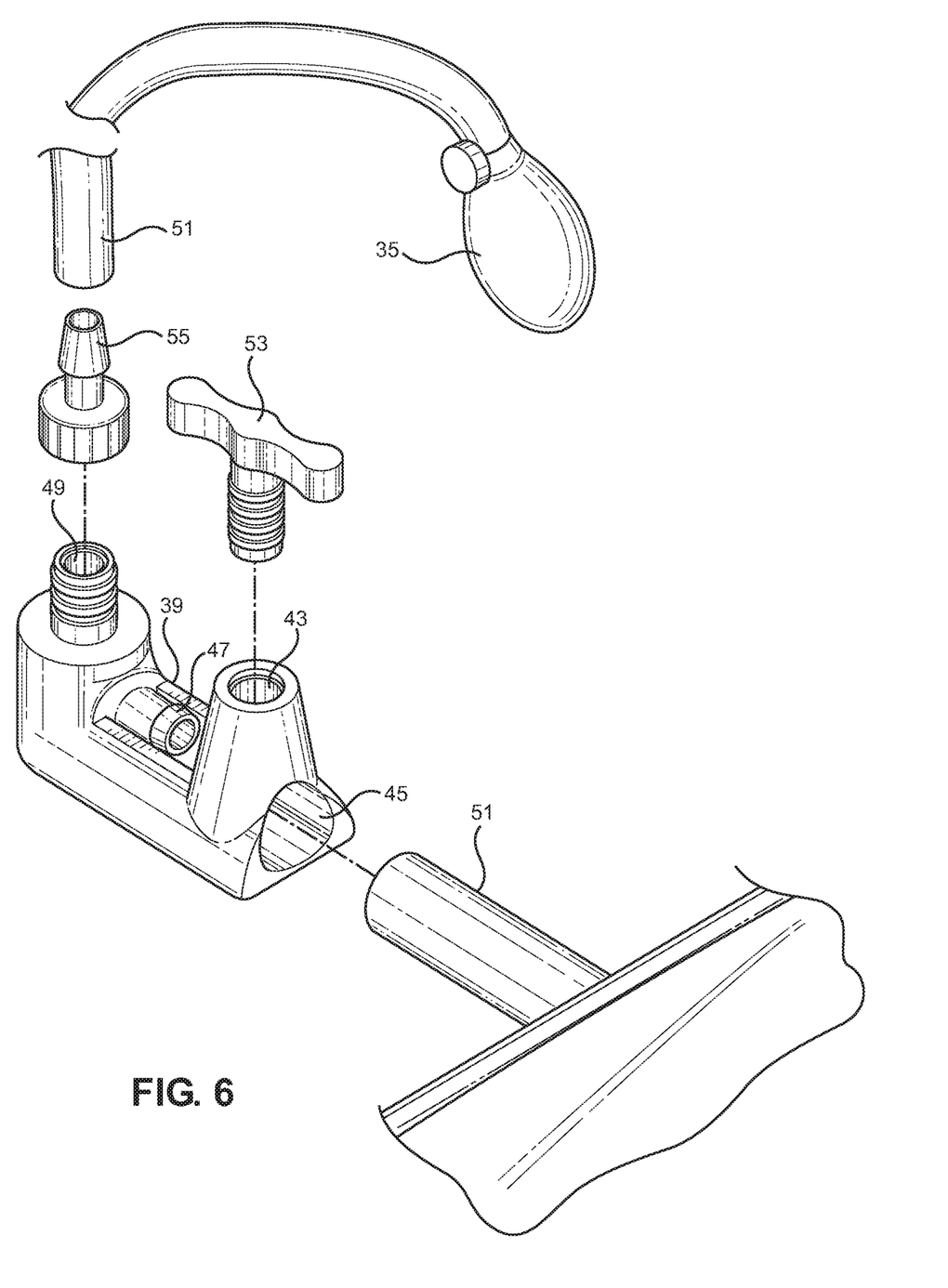
FIG. 6 shows an exploded view of a preferred valve system of an embodiment of the present invention.

The top layer 25 further comprises a valve 33 to permit the inflation and/or deflation of the second void 23 with air. The valve 33 can be attachable to a pump 35, or, optionally, can be inflatable by mouth, or can be of any other type known to the art for selectable inflation and deflation. As would be appreciated by one skilled in the art, suitable materials for the valve 33 would include any material commonly used in the art that is impermeable to air, such as metal or polymer. In a preferred embodiment, the valve 33 comprises a valve base 39 with a first aperture 43 oriented orthogonally to the length of the valve base 37 and a second aperture 45 coupled to the first aperture 43 and oriented coaxially to the valve base 39. The valve base 39 further comprises a tubular first member 47 oriented coaxially to the length of the valve base 37 and substantially aligned with the second aperture 45. A tubular second member 49 is coupled to the first member 47, and a tube insert 55 is removably coupled to the second member 49.

In use, tubing 51 that is coupled at one end to the inflatable air bladder 31 is inserted through the second aperture 45 and removably coupled to the first member 47. Tubing 51 that is coupled at one end to a pump 35 is removably coupled to the tube insert 55, which is removably coupled to the second member 49. The inflatable air bladder 31 may then be inflated to a desired pressure by pumping air using the pump 35, wherein the air flows in a direction from the pump 35, through the tubing 51 coupled to the pump 35, through the tube insert 55, the second member 49, and the first member 47, and then through the tubing 51 coupled to the first member 47, and ultimately, into the inflatable air bladder 31. The selected air pressure inside the inflatable air bladder 31 may then be substantially maintained by inserting a plug member 53 into the first aperture 43 to compress the portion of the tubing 51 that is inserted through the second aperture 45, thus substantially restricting air flow in either direction through the tubing 51 coupled to the inflatable air bladder 31. As would be appreciated by one skilled in the art, the plug member 53 may be secured inside the first aperture 43 by any means commonly used in the art, but the plug member 53 is preferably secured inside the first aperture 43 with threading on the outer surface of the plug member 53 and corresponding threading on the inner surface of the first aperture 43. Optionally, the top layer 25 may further comprise an integral pump 35 for inflation of the inflatable air bladder 31.

The bottom layer 1, middle layer 11, and top layer 25 are joined and sealed at their top and bottom edges, resulting in the first void 7 and second void 23 generally comprising closed, substantially impermeable, annular containers, and further resulting in a device with the general form of an open sleeve or cylinder.

Figure 1:
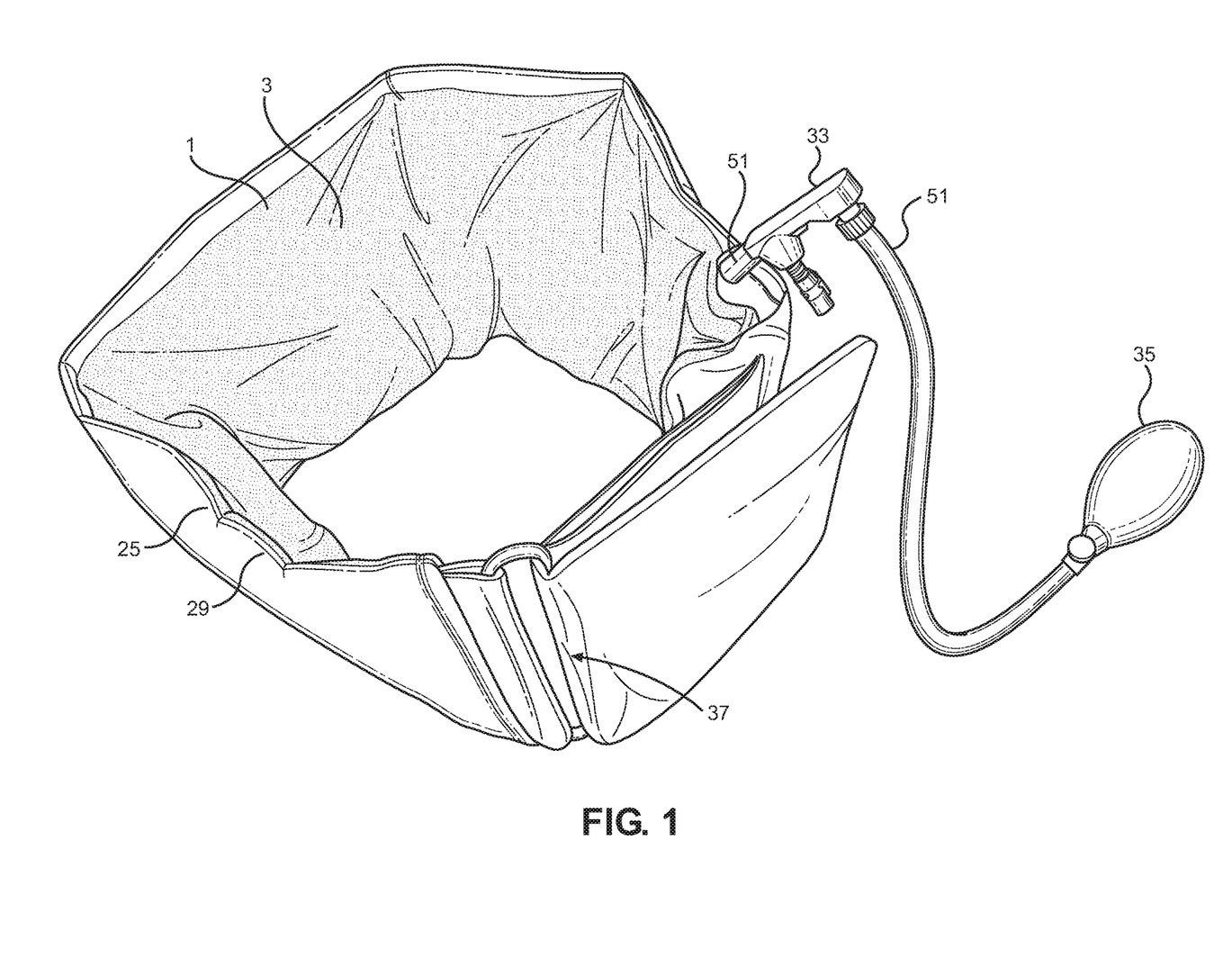
FIG. 1 shows a perspective view of an embodiment of the present invention.
Figure 2:
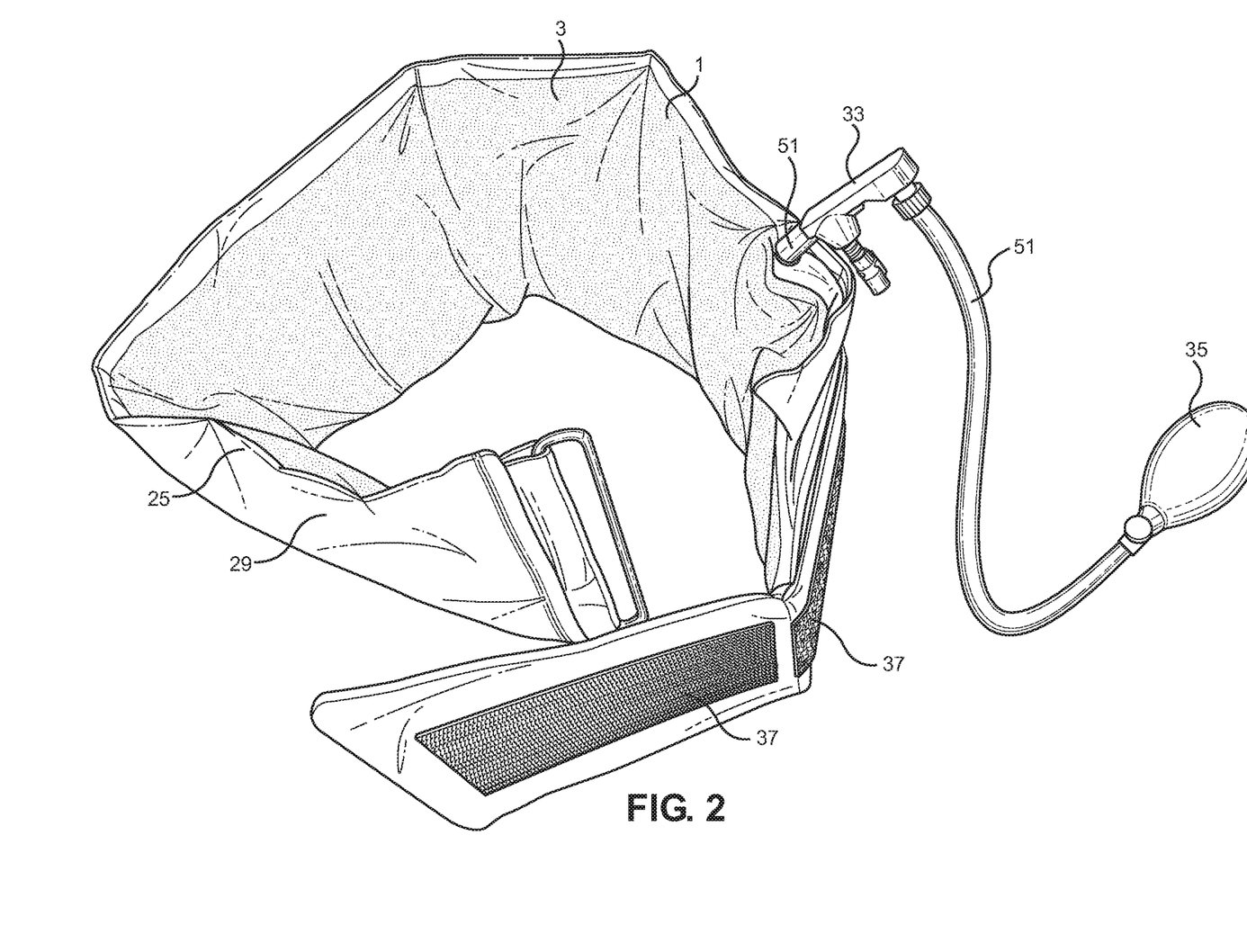
FIG. 2 shows a perspective view of an unattached embodiment of the present invention.
Figure 3:
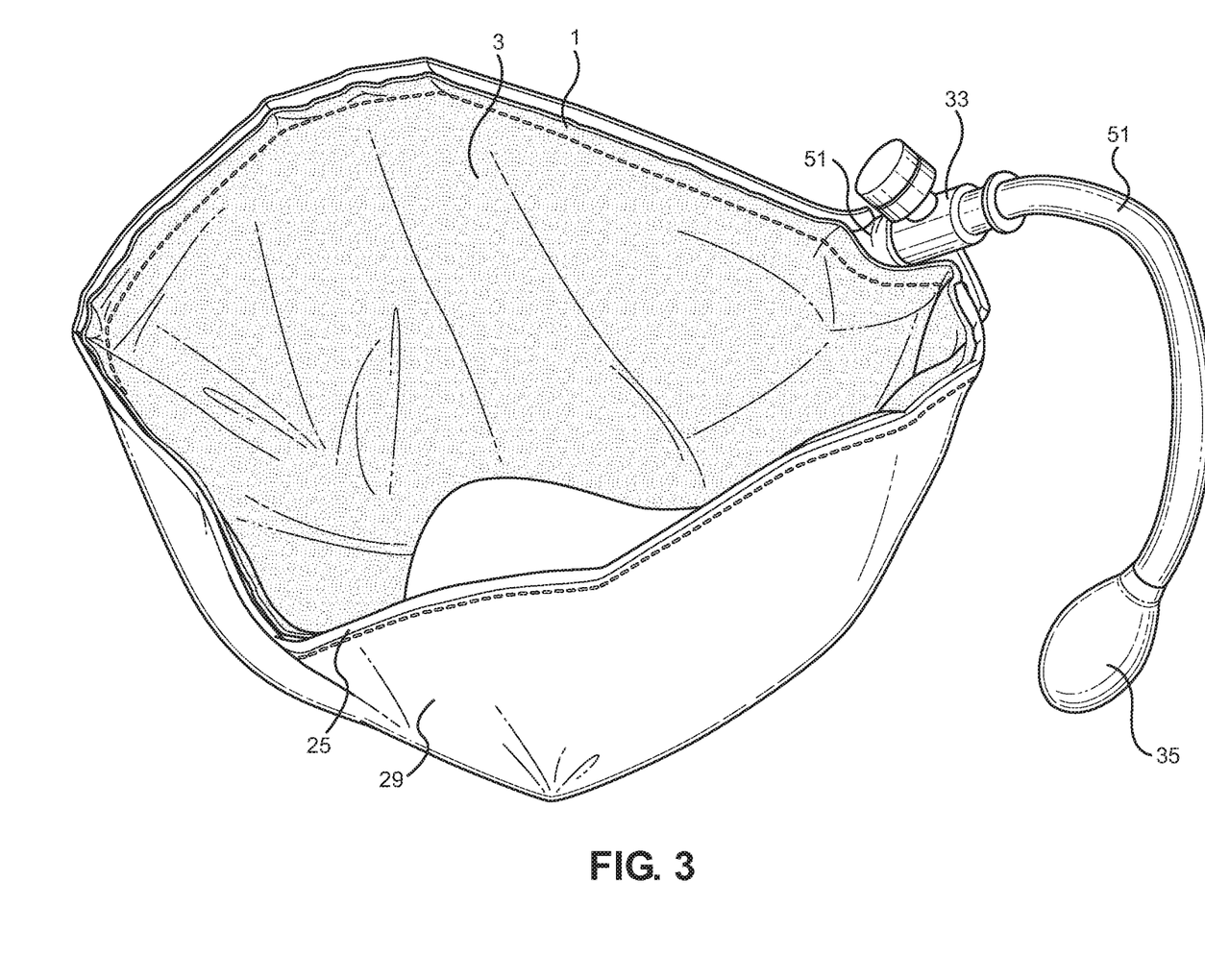
FIG. 3 shows a perspective view of an embodiment of the present invention.
Figure 4:
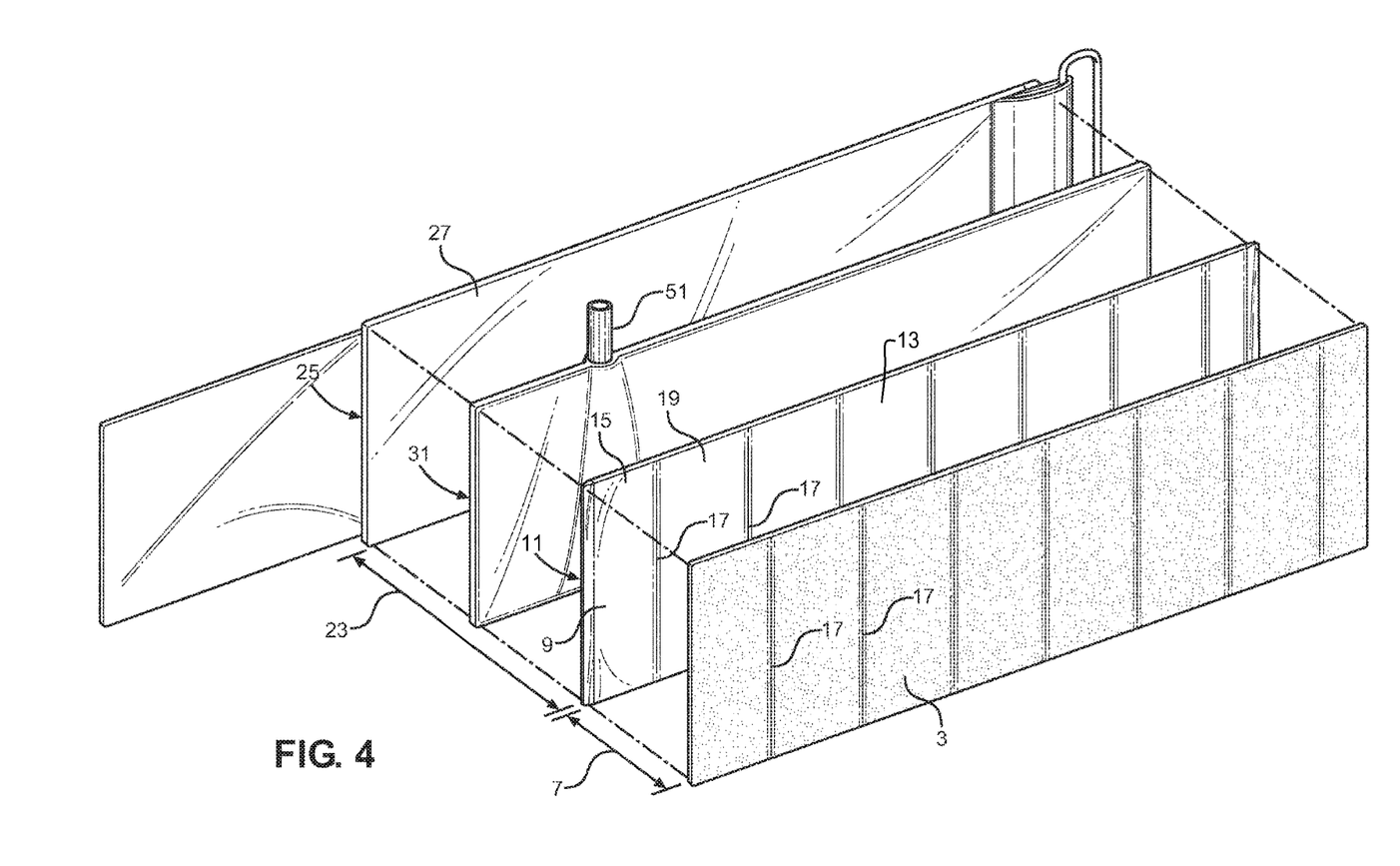
FIG. 4 shows an exploded view from the inside of an embodiment of the present invention.
Figure 5:
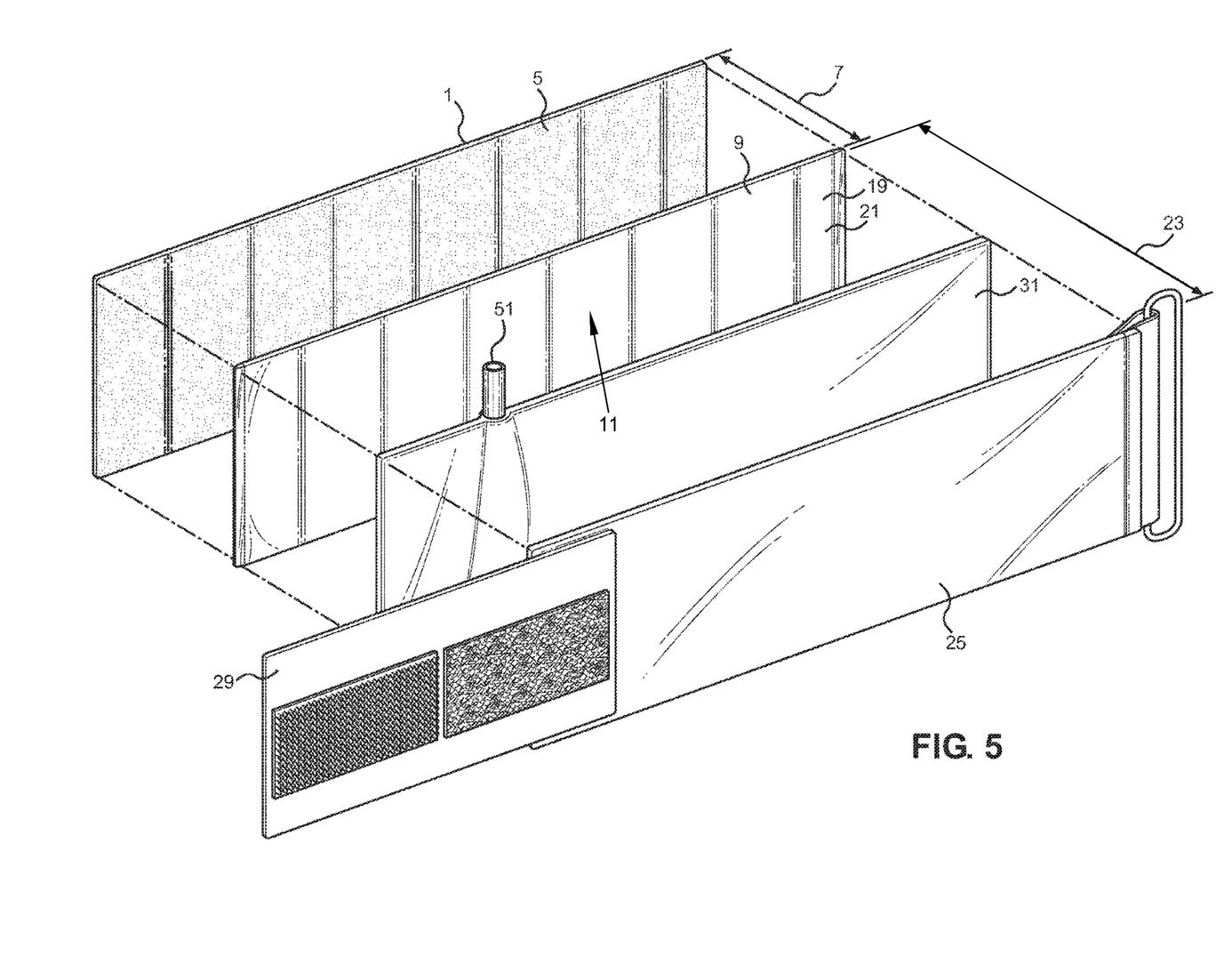
FIG. 5 shows an exploded view from the outside of an embodiment of the present invention.

While the device as described in the embodiments above is a unitary sleeve, in alternate embodiments, the device may comprise a detachable sleeve in the nature of a blood pressure cuff. In these detachable sleeve embodiments, the device when not in use forms a flat, generally rectangular sheet. The sixth surface 29 in these embodiments further comprises a fastening means 37 for fastening the relatively flat sheet of the device to itself to form an annular structure in the nature of a sleeve or ring. In further alternate embodiments, such as ones used to treat an injured shoulder, the device may comprise a sleeve coupled to additional cooling portions that, when in use, are wrapped around the user's torso and optionally secured in place by a fastening means 37. Suitable fastening means 37 for any embodiment include hook-and-loop fasteners, buttons, zippers, adhesives, snaps, and other mechanical and clothing fasteners as would be appreciated by one skilled in the art.

A user employs the device by activating the cooling agent 9 (by, for example, placing the device in a refrigerator or freezer to cool a reusable cooling agent 9, or by chemically activating a disposable cooling agent 9) until the device is of a desired temperature for cooling therapy. With the second void 23 substantially deflated, the user slips the limb desired to be treated into the sleeve and places the device on a limb over the joint or site targeted for treatment. The user then inflates the second void 23 until the device is compressed to a desired pressure. The valve 33 is then closed. In this way, the user has the use of both hands and substantially full mobility while cooling therapy is being applied. The device further suffers few to none of the hygiene and discomfort drawbacks of other cooling therapy strategies known to the art, and applies cooling therapy to the entire circumferential area of the target joint or site.

In another embodiment, a user employs the device by activating the cooling agent 9 (by, for example, placing the device in a refrigerator or freezer to cool a reusable cooling agent 9, or by chemically activating a disposable cooling agent 9) until the device is of a desired temperature for cooling therapy. With the second void 23 substantially deflated, the user wraps the device around the limb desired to be treated over the joint or site targeted for treatment and fastens the device to itself to form a sleeve over the desired treatment site. The user then inflates the second void 23 until the device is compressed to a desired pressure. The valve 33 is then closed. In this way, the user has the use of both hands and substantially full mobility while cooling therapy is being applied. The device further suffers few to none of the hygiene and discomfort drawbacks of other cooling therapy strategies known to the art, and applies cooling therapy to the entire circumferential area of the target joint or site.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A cooling compression sleeve device for providing therapy to limbs, said device comprising:
   a flexible bottom layer comprising a first surface and a second surface opposite said first surface;
   an interior first void facing said second surface and forming a closed container that is only filled with a liquid cooling agent, wherein said second surface is impermeable to said cooling agent and said cooling agent is in contact with said second surface;
   a flexible middle layer comprising a third surface facing said first void and a fourth surface opposite said third surface, wherein said third surface is impermeable to said cooling agent, and wherein said fourth surface is impermeable to air;
   an interior second void facing said fourth surface, wherein said second void comprises a selectively inflatable air bladder;
   a flexible top layer comprising a fifth surface facing said second void and a sixth surface opposite said fifth surface, wherein said fifth surface is impermeable to air, wherein said sixth surface faces an outer environment; and
   a valve coupled to said air bladder, wherein said valve is removably attachable to tubing, and wherein said tubing is coupled to a pump, wherein said valve comprises a valve base with a first aperture oriented orthogonally to the length of said valve base and a second aperture coupled to said first aperture and oriented coaxially to the valve base, wherein said valve base further comprises a tubular first member oriented coaxially to the length of said valve base and substantially aligned with said second aperture, wherein a tubular second member is coupled to said tubular first member, and wherein a tube insert is removably coupled to said tubular second member, wherein said tubular second member extends orthogonally with said tubular first member.

2. The device of claim 1, wherein said bottom layer comprises a material with high thermal conductivity.

3. The device of claim 2, wherein said first surface comprises a water absorbent material.

4. The device of claim 3, wherein said water absorbent material comprises one or more of cotton, microfiber, and a cotton/microfiber mixture.

5. The device of claim 1, wherein said second surface, said third surface, and said fourth surface each comprise at least one of flexible silicone or neoprene.

6. The device of claim 1, wherein said first void comprises the entirety of the volume between said second surface of said bottom layer and said third surface of said middle layer.

7. The device of claim 1, wherein said first void comprises one or more chambers divided by walls, wherein each wall connects said second surface to said third surface.

8. The device of claim 1, wherein said cooling agent is reusable.

9. The device of claim 8, wherein said cooling agent comprises at least one of a water-propylene glycol mixture or a water-antifreeze mixture.

10. The device of claim 1, wherein said middle layer insulates said cooling agent from environmental or atmospheric heat external to said first void.

11. The device of claim 1, wherein said sixth surface is adapted to resist abrasions and collisions and further adapted to resist punctures of said second void or said first void.

12. The device of claim 11, wherein said top layer comprises nylon.

13. The device of claim 1, further comprising tubing coupled at one end to the inflatable air bladder and inserted at another end through the second aperture and removably coupled to said first member, and further comprising tubing coupled at one end to said pump and removably coupled at another end to said tube insert.

14. The device of claim 13, further comprising a plug member, wherein said plug member is securably insertable into said first aperture and adapted to restrict air flow in either direction through the tubing coupled to said inflatable air bladder and inserted through said second aperture.

15. The device of claim 1, wherein said device comprises a detachable sleeve comprising a generally flat rectangular sheet, and wherein said sixth surface further comprises a fastener configured to fasten the relatively flat sheet of the device to itself to form an annular structure in the form of a sleeve or ring.

16. The device of claim 14, wherein said plug member is movable within said first aperture from a first member position to a second member position, said plug member being configured to compress said tubing and restrict air flow through said tubing when in said first member position and to allow air flow through said tubing when in said second member position.

17. The device of claim 16, wherein said plug member includes a plurality of threads configured to secure said plug member within said first aperture.

18. The device of claim 16, wherein said plug member comprises an insertion portion insertable within said first aperture and a handle portion coupled to and extending orthogonally from said insertion portion.

* * * * *